US00PP12288P2

(12) United States Plant Patent
Stemkens

(10) Patent No.: US PP12,288 P2
(45) Date of Patent: Dec. 18, 2001

(54) VERBENA PLANT NAMED 'VERTIS'

(75) Inventor: Henricus G. W. Stemkens, Hoorn (NL)

(73) Assignee: Syngenta Seeds B.V., Enkhuisen (NL)

( * ) Notice: Subject to any disclaimer, the term of this patent is extended or adjusted under 35 U.S.C. 154(b) by 2 days.

(21) Appl. No.: 09/615,371

(22) Filed: Jul. 13, 2000

(51) Int. Cl.[7] ..... A01H 5/00

(52) U.S. Cl. ..... Plt./308

(58) Field of Search ..... Plt./308

*Primary Examiner*—Bruce R. Campell
*Assistant Examiner*—June Hwu
(74) *Attorney, Agent, or Firm*—Bruce Vrana

(57) ABSTRACT

A new Verbena plant particularly distinguished by its large white flower, early flowering, no seed set, and a semi-erect habit that becomes spreading as plant develops.

1 Drawing Sheet

BACKGROUND OF THE NEW PLANT

The present invention comprises a new distinct cultivar of Verbena, botanically known as *Verbena×hybrida*. The new cultivar is propagated from cuttings resulting from the cross of 'U1022' 'T1183'. 'U1022' is a white flowering Verbena having a spreading habit. 'U1022' is not commercially available and is not known by any synonyms. 'T1183' is a white flowering Verbena having a semi-erect habit. 'T1183' is not commercially available and is not known by any synonyms. Neither 'U1022' or 'T1183' has been patented. As as a result of this cross the present cultivar was created in 1996 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

This new Verbena plant is an annual in most climatical zones in the US, only in zones 9 and 10 it is a perennial plant.

DESCRIPTION OF THE DRAWING

This new Verbena plant is illustrated by the accompanying photographic drawings which show blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new Verbena. The data which defines these characteristics were collected from asexual reproductions carried out in Enkhuizen, Netherlands. The plant history was taken on 14 weeks old plants, blossomed under natural light in a greenhouse. Color readings were taken in the greenhouse under ambient light. Color references are primarily to The R.H.S. Color Chart of The Royal Horticultural Society of London.

Differences between the new variety 'Vertis', its parents and a similar cultivar

| | Character | | | |
|---|---|---|---|---|
| | 'Vertis' | 'U1022' | 'T1183' | 'Temari white' |
| Seed set | No | No | Yes | Yes |
| Leaf form | Pinnatifid | Pinnatifid | Oblong | Ovate |
| Flower size | 14–16 mm | 10–12 mm | 16–18 mm | 20–23 mm |

The Plant

Classification — Botanical: *Verbena×hybrida.*
Parentage:
*Female parent.*—A seedling named 'U1022' is one of our seedlings from our U-generation of plant bred in 1991.
*Pollen parent.*—A seedling named 'T1183' is one of our seedlings from our T-generation of plants bred in 1990.
Growth habit: Semi-erect, later spreading.
Plant height: 18–28 cm.
Spreading area of plant: 40–80 cm.
Growth rate: Vigorous.
Strength: Very good.
Branching character: Freely branching and lateral branching at every node.
Blooming period: From April until November.

The Stem

Diameter: 2–2.5 mm.
Shape: Tetragonal.
Color: 141C.
Anthocyan pigmentation: Absent.
Length of internode: 35–65 mm, depending on the light where the plant is propagated.
Pubescence: Slightly pubescent.

The Foliage

Phyllotaxis: Opposite.
Shape of blade: Broadly ovate.

Texture:
*Upper side.*—Slightly pubescent.
*Lower side.*—Slightly pubescent.
Venation: Pinnate.
Leaf margin: Biserrate and irregularly incised.
Leaf base: Attenuate.
Leaf apex: Acute.
Length: 20–45 mm.
Width: 18–36 mm.
Depth of incision: 10–20 mm.
Color:
*Upper side.*—Dark green 139A.
*Lower side.*—Medium green 141A.
Pubescence: Some pubescence is present.
Length of petiole: 5–15 mm.
Color of petiole: Light green 141C.
Petiole surface texture: Slightly pubescent.

The Bud

Peduncle length: 40–70 mm, depending on season.
Size:
*Diameter.*—2 mm.
*Length.*—8–12 mm.
Shape: Elongated and ovate.
Color: Medium green 141A.
Sepals:
*Color.*—Light green 137D.
*Form.*—Upright.
*Number.*—5, fused.
*Size.*—7 mm.
*Shape.*—Elongated.

The Flower

Direction: Ascending.
Diameter: 14–16 mm.
Corolla tube length: 16–18 mm.
Borne: In a cluster.
Form: Salverform; sessile on terminal spikes.
Cluster: Spike.
Color: White 155D.
Eye: A very small (2 mm) green-white eye (157C) is present. The three lower petals exhibit this green-white coloration at their bases.
Overlapping of petals: Separate.
No. of petals: Gamopetalous, five lobed.
Shape of the petals: Each petal is irregularly heart-shaped at the apex and grown together at the base.
Petal margin: Irregularly crenate.
Petal surface texture: Smooth.
Size of the petal:
*Length.*—6–8 mm.
*Width.*—5–7 mm.
Spike:
*Length.*—40–70 mm.
*Diameter.*—30–45 mm.
Calyx: Length of 10–12 mm.
Anthocyan pigmentation of calyx limb: Absent.
No. of flowers per spike: 40–65.
Fragrance: No fragrance.
Lastingness of the bloom: New florets continue to open in one spike over a period of 20 days.
Reproductive organs: One pistil and four stamens in pairs; color for both is yellow green 150D. The pistil size is 15–17 mm in length. Pollen is present with a color of yellow 5D. The filaments and anthers are fused to the corolla. The anthers are enclosed and not a prominent feature of the flower. 'Vertis' does not freely set seed.
Roots:
*Type of roots.*—Fibrous. Roots start to grow on every part of the stem that contacts the soil, so not only at the nodes.
Physiological and ecological characteristics: Good tolerance to heat and cold. Strong resistance to pests and diseases, particularly powdery mildew.

What is claimed is:

1. A new and distinct variety of Verbena plant, substantially as herein illustrated and described, characterized particularly as to novelty by white flowers, which appear earlier on the plant, and has a growing habit that is first semi-erect but later spreading and hanging.

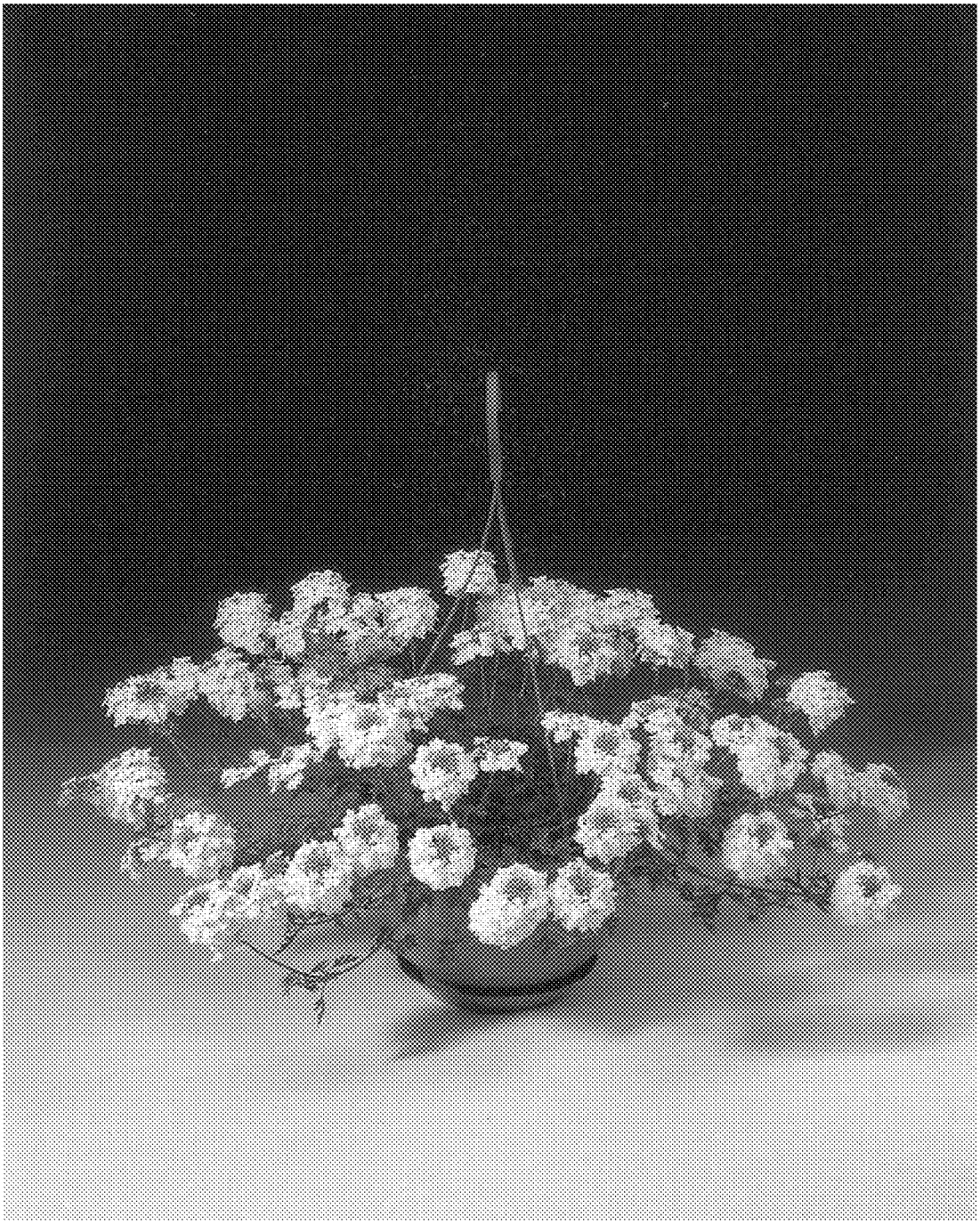

* * * * *